US012079989B2

United States Patent
Mavroeidis et al.

(10) Patent No.: US 12,079,989 B2
(45) Date of Patent: Sep. 3, 2024

(54) IDENTIFYING BOUNDARIES OF LESIONS WITHIN IMAGE DATA

(71) Applicant: KONINKLIJKE PHILIPS N.V., Eindhoven (NL)

(72) Inventors: Dimitrios Mavroeidis, Utrecht (NL); Stojan Trajanovski, London (GB); Bart Jacob Bakker, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 338 days.

(21) Appl. No.: 17/600,405

(22) PCT Filed: Apr. 3, 2020

(86) PCT No.: PCT/EP2020/059583
§ 371 (c)(1),
(2) Date: Sep. 30, 2021

(87) PCT Pub. No.: WO2020/201516
PCT Pub. Date: Oct. 8, 2020

(65) Prior Publication Data
US 2022/0180516 A1    Jun. 9, 2022

(30) Foreign Application Priority Data
Apr. 4, 2019   (EP) .................................. 19167213

(51) Int. Cl.
*G06T 7/00*    (2017.01)
*G06T 7/12*    (2017.01)
(Continued)

(52) U.S. Cl.
CPC .............. *G06T 7/0012* (2013.01); *G06T 7/12* (2017.01); *G06T 7/187* (2017.01); *G06T 7/70* (2017.01);
(Continued)

(58) Field of Classification Search
CPC ......... G06T 7/0012; G06T 7/12; G06T 7/187; G06T 7/70; G06T 2207/20076;
(Continued)

(56) References Cited

U.S. PATENT DOCUMENTS

2007/0081712 A1   4/2007   Huang et al.
2014/0247977 A1   9/2014   Han
(Continued)

FOREIGN PATENT DOCUMENTS

CN   107730507 A   2/2018
WO   2008002633 A2  1/2008
(Continued)

OTHER PUBLICATIONS

Zhu et al: "A Bayesian Model for Fusing Biomedical Labels"; Semantic Scholar, Chapter 7, pp. 127-159, 2016.
(Continued)

*Primary Examiner* — Casey L Kretzer
(74) *Attorney, Agent, or Firm* — Sherry Austin

(57) ABSTRACT

The present invention provides a method, computer program and processing system for identifies boundaries of lesions within image data. The image data is processed using a machine learning algorithm to generate probability data and uncertainty data. The probability data provides, for each image data point of the image data, a probability data points indicating a probability that said image data point is part of a lesion. The uncertainty data provides, for each probability data point, an uncertainty data point indicating an uncertainty of the said probability data point. The uncertainty data is processed to identify or correct boundaries of the lesions.

20 Claims, 4 Drawing Sheets

(51) Int. Cl.
*G06T 7/187* (2017.01)
*G06T 7/70* (2017.01)
*G06V 10/70* (2022.01)
*G16H 30/40* (2018.01)
*G16H 50/20* (2018.01)

(52) U.S. Cl.
CPC .............. *G06V 10/70* (2022.01); *G16H 30/40* (2018.01); *G16H 50/20* (2018.01); *G06T 2207/20076* (2013.01); *G06T 2207/20081* (2013.01); *G06T 2207/20084* (2013.01); *G06T 2207/20092* (2013.01); *G06T 2207/30096* (2013.01)

(58) Field of Classification Search
CPC . G06T 2207/20081; G06T 2207/20084; G06T 2207/20092; G06T 2207/30096; G06V 10/70; G16H 30/40; G16H 50/20
See application file for complete search history.

(56) References Cited

U.S. PATENT DOCUMENTS

2017/0098301 A1* 4/2017 Ikemoto ................ G06T 7/0012
2017/0287134 A1 10/2017 Abedini et al.

FOREIGN PATENT DOCUMENTS

WO 2018156778 A1 8/2018
WO 2018222755 A1 12/2018

OTHER PUBLICATIONS

Hoogi et al: "Adaptive Estimation of Active Contour Parameters Using Convolutional Neural Networks and Textures Analysis"; IEEE Transactions on Medical Imaging, vol. 35, No. 3, Mar. 2017, pp. 781-791.
PCT/EP2020/059583—ISR & Written Opinion, Jul. 16, 2020.
Kendall et al: "What Uncertainties Do We Need in Bayesian Deep Learning for Computer Vision?"; 31st Conference on Neural Information Processing Systems (NIPS 2017), Long Beach, CA, USA, pp. 1-12.
Litjens et al: "A Survey on Deep Learning in Medical Image Analysis"; Medical Image Analysis, 42 (2017), pp. 60-88.
Norouzi et al: "Medical Image Segmentation Methods, Algorithms, and Applications"; Medical Image Segmentation Methods, Algorithms, and Applications, IETE Technical Review, 31:3, pp. 199-213, 2014.
Salehi et al: "Tversky Loss Function for Image Segmentation Using 3D Fully Convolutional Deep Networks"; arXiv:1706.05721v1, Jun. 18, 2017, 9 Page Document.

* cited by examiner

IDENTIFYING BOUNDARIES OF LESIONS WITHIN IMAGE DATA

CROSS-REFERENCE TO PRIOR APPLICATIONS

This application is the U.S. National Phase application under 35 U.S.C. § 371 of International Application No. PCT/EP2020/059583, filed on Apr. 3, 3030, which claims the benefit of European Patent Application No. 19167213.8, filed on Apr. 4, 2019. These applications are hereby incorporated by reference herein.

FIELD OF THE INVENTION

The present invention relates to the field of automated processing of a medical image, and in particular, to the identifying of boundaries of lesions within image data for the medical image.

BACKGROUND OF THE INVENTION

There has been an increasing interest in the use of machine-learning algorithms to analyze medical images. In particular, machine-learning algorithms have the potential to perform highly accurate medical image segmentation tasks, such as organ segmentation, nodule segmentation and so on. One area of particular interest is using machine-learning algorithms to identify lesions within a medical image, such as a CT (computed tomography) scan, ultrasound image or X-ray image.

A challenge of implementing machine-learning algorithms is that the training data used to train the machine-learning algorithm may not be fully accurate, e.g. due to incorrect or incomplete annotations by a trained clinician. Inaccurate annotation of lesions is particularly prevalent at the boundaries of the lesions, where a clinician may be unable or unwilling to accurate identify the precise boundaries of a lesion. This problem is exacerbated by the fact that these often inaccurate/ambiguous lesion annotations need to be resampled to a uniform resolution to allow for training of the machine-learning algorithm. The need to upsample lower resolution images and ambiguous/inaccurate annotations results in less accurate training data for the machine-learning algorithm.

Moreover, different boundary-identifying machine-learning algorithms, processing a same image, may identify different boundaries of a lesion, e.g. due to differences in the training data or loss function used to train the machine-learning annotating algorithm. Thus, there may be disagreement between different annotating algorithms in precisely where a boundary of a lesion lies.

The inventors have recognized that there is therefore a need to improve the identification of the boundaries of lesions within medical images. Improved identification of the boundaries of lesions provides a clinician with more accurate information, thereby enabling them to diagnose or assess a subject with greater accuracy.

SUMMARY OF THE INVENTION

The invention is defined by the claims.

According to examples in accordance with an aspect of the invention, there is provided a method of identifying one or more boundaries of lesions within N-dimensional medical image data of a region of a subject.

The method comprises: receiving the N-dimensional medical image data, comprising image data points; processing the N-dimensional medical image data, using a machine-learning algorithm, to thereby generate: N-dimensional probability data, comprising a respective probability data point for each image data point indicating a probability that the image data point is part of a lesion; and N-dimensional uncertainty data, comprising a respective uncertainty data point for each probability data point indicating an uncertainty of the indicated probability; and identifying one or more boundaries of lesions in the medical image data using at least the uncertainty data.

The invention proposes to identify boundaries of lesions within (medical) image data based upon uncertainty data. The uncertainty data comprises uncertainty data points. Each uncertainty data point indicates an uncertainty of a predicted probability associated with a particular image data point. The predicted probability is a prediction as to whether that particular image data point is part of a lesion (e.g. on a scale of 0-1), i.e. "lesion probability".

The probability data can be used to predict the location, size and shape of a lesion. For example, if a cluster of image data points are each associated with probability data indicating that each of the cluster has a certain probability (above a predetermined value) that it is part of a lesion, then that cluster of image data points can be considered a predicted lesion. Such methods would be well known to the skilled person.

The present invention relies on the understanding that the probability data may not be completely accurate when predicting whether a given image data point is part of a lesion or not. Indeed, the present invention identifies that the level of accuracy reduces near the boundary or edge of a lesion.

The inventors have recognized that uncertainty data can be used to more accurately identify where a boundary of a lesion lies with respect to the image data. In particular, uncertainty of a lesion probability can be used in the discrimination or determination of where a boundary or edge of a lesion lies. Thus, the problem of inaccurately trained machine-learning algorithms can be overcome by using uncertainty data to modify, identify or correct boundaries of lesions. These inaccuracies are particularly prevalent at borders of lesions.

The proposed invention thereby enables more accurate identification of boundaries of lesions. This directly aids a user in the performance of a task of diagnosing or assessing a condition of the subject, as there will be more accurate identification of the number, location and size of lesions within the subject. In particular, knowledge of the extent and location of lesions is essential for correctly analyzing a condition of a subject.

The step of identifying one or more boundaries of lesions may comprise: identifying one or more potential lesions in the medical image data based on the probability data; and processing each potential lesion using at least the uncertainty data to identify one or more boundaries of lesions in the medical image data.

Boundaries of lesions can therefore be identified by identifying potential lesions in the medical image data and using at least the uncertainty data to correct or modify the boundaries of the identified potential lesion.

The step of identifying one or more potential lesions in the medical image data may comprise identifying groups of image data points associated with a probability data point that indicates that a probability that the image data point is part of a lesion is above a predetermined probability, each group of image data points thereby forming a potential lesion. Thus, clusters of image data points form a potential lesion, if each image data point in the cluster is associated with a sufficiently high (above a predetermined threshold) probability of being part of a lesion.

Embodiments may comprise a step of selectively rejecting (i.e. excluding from further consideration) potential lesions based on the uncertainty data. For example, if image data points forming a potential lesion are associated with an average uncertainty above a predetermined value, the potential lesion may be rejected (i.e. removed from the one or more potential lesions). As another example, if more than a certain percentage of image data points forming a potential lesion are associated with an uncertainty data point having an uncertainty above a predetermined value, then this potential lesion can be rejected.

Thus, uncertain potential lesions may be rejected. In this way, potential lesions can be rejected based on the uncertainty data. This improves the accuracy in correctly identifying potential lesions, in particular the true positive rate, by rejecting those lesions that are uncertainly predicted.

In some embodiments, the step of identifying one or more boundaries of lesions comprises processing the image data, the probability data and the uncertainty data using a region growing algorithm to thereby identify one or more boundaries of lesions.

Region growing methods can be used to appropriately expand or reduce a predicted lesion by using a set of rules to decide whether neighboring image data points should be added to the predicted lesion.

Region growing rules can be based on image features of the image data, such as the magnitude (e.g. Hounsfield Unit or HU) of an image data point, with the decision rule being a simple threshold on the image data point's magnitude.

In particular, the inclusion threshold may be based on the level of uncertainty for the same image data point. In particular, the inclusion threshold may be generated by the machine-learning algorithm, e.g. based upon a calculated uncertainty for the image data point. As another example, the level of uncertainty may weight an inclusion value.

Similarly, these rules can be used to reduce the size of a lesion, for example by inspecting the voxels that are included in the perimeter of the lesion and applying the decision rules that combine the image data point magnitude and uncertainty thresholds.

There are therefore embodiments in which identifying one or more boundaries of lesions comprises applying a region growing algorithm and/or a region shrinking algorithm to each potential lesion.

The region growing algorithm may comprise iteratively performing steps of: identifying perimeter image data points that form the perimeter of the potential lesion; identifying neighboring image data points, being image data points external to the potential lesion and immediately adjacent to any of the perimeter image data points; and for each neighboring image data point, adding the neighboring image data point to the potential lesion in response to a magnitude of the neighboring image data point being greater than a first magnitude threshold value for that neighboring image data point, wherein the first magnitude threshold value is based upon the uncertainty data point associated with the neighboring image data point, wherein the first region growing algorithm ends in response to no new neighboring image data points being identified.

The region shrinking algorithm may comprise iteratively performing steps of: identifying perimeter image data points that form the perimeter of the potential lesion; for each perimeter image data point, removing the perimeter image data point from the potential lesion in response to a magnitude of the perimeter image data point being less than a second magnitude threshold value for the perimeter image data point, wherein the second magnitude threshold value is based upon the uncertainty data point associated with the perimeter image data point, wherein the second region growing algorithm ends in response to no new perimeter image data points being identified.

The step of identifying one or more boundaries of lesions may comprise: identifying one or more predicted boundary portions of each potential lesion using the probability data, each predicted boundary portion being a predicted location of a portion of a boundary of the potential lesion; identifying an uncertainty of each predicted boundary portion and/or an uncertainty of each potential lesion using the uncertainty data; selecting one or more of the predicted boundary portions based on the identified uncertainty of each boundary portion and/or an uncertainty of each potential lesion; presenting the selected predicted boundary portions to a user; after presenting the selected predicted boundary portions to the user, receiving a user input indicating one or more boundaries of lesions; and identifying the boundary portions based on the received user input.

Optionally, the step of selecting one or more predicted boundary portions comprises selecting those boundary portions associated with an uncertainty below a first predetermined uncertainty value and/or those boundary portions associated with a lesion having an uncertainty below a second predetermined uncertainty value.

The method may further comprise generating a respective one or more graphical annotations, each indicating a location of each one or more identified boundaries.

Preferably, the machine-learning algorithm is a Bayesian deep learning segmentation algorithm. A Bayesian deep learning segmentation algorithm can be readily adapted to generate uncertainty data, and therefore provides an appropriate machine-learning algorithm for processing the image data. In preferred embodiments, the image data is computed tomography, CT, image data. In some embodiments, N is equal to 3. In such embodiments, the term "N-dimensional" may be replaced by the term "3-dimensional" (3D).

There is also proposed computer program comprising code means for implementing any described method when said program is run on a processing system.

According to examples in accordance with an aspect of the invention, there is also provided a processing system for identifying one or more boundaries of lesions within N-dimensional medical image data of a region of a subject. The processing system is adapted to: receive the N-dimensional medical image data, comprising image data points; process the N-dimensional medical image data, using a machine-learning algorithm, to thereby generate: N-dimensional probability data, comprising a respective probability data point for each image data point indicating a probability that the image data point is part of a lesion; and N-dimensional uncertainty data, comprising a respective uncertainty data point for each probability data point indicating an uncertainty of the indicated probability; and identify one or more boundaries of lesions in the medical image data using at least the uncertainty data.

The processing system may be adapted to identify one or more boundaries of lesions by identifying one or more potential lesions in the medical image data based on the probability data; and processing each potential lesion using at least the uncertainty data to identify one or more boundaries of lesions in the medical image data.

In some embodiments, the processing system may be adapted to process each potential lesion by processing the image data, the probability data and the uncertainty data using a region growing algorithm to thereby identify one or more boundaries of lesions.

In other embodiments, the processing system may be adapted to process each potential lesion by: identifying one or more predicted boundary portions using the probability data, each predicted boundary portion being a predicted location of a portion of a boundary of a lesion; identifying an uncertainty of each predicted boundary portion using the uncertainty data; selecting one or more of the predicted boundary portions based on the identified uncertainty of each boundary portion; presenting the selected predicted boundary portions to a user; after presenting the selected predicted boundary portions to the user, receiving a user input indicating one or more boundaries of lesions; and identifying the boundary portions based on the received user input.

The processing system may be adapted to select one or more predicted boundary portions by selecting those boundary portions associated with an uncertainty below a predetermined uncertainty value.

In some embodiments, the processing system is further adapted to generate a respective one or more graphical annotations, each indicating a location of each one or more identified boundary.

The machine-learning algorithm may be a Bayesian deep learning segmentation algorithm.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings.

DETAILED DESCRIPTION OF THE EMBODIMENTS

Figure 1:
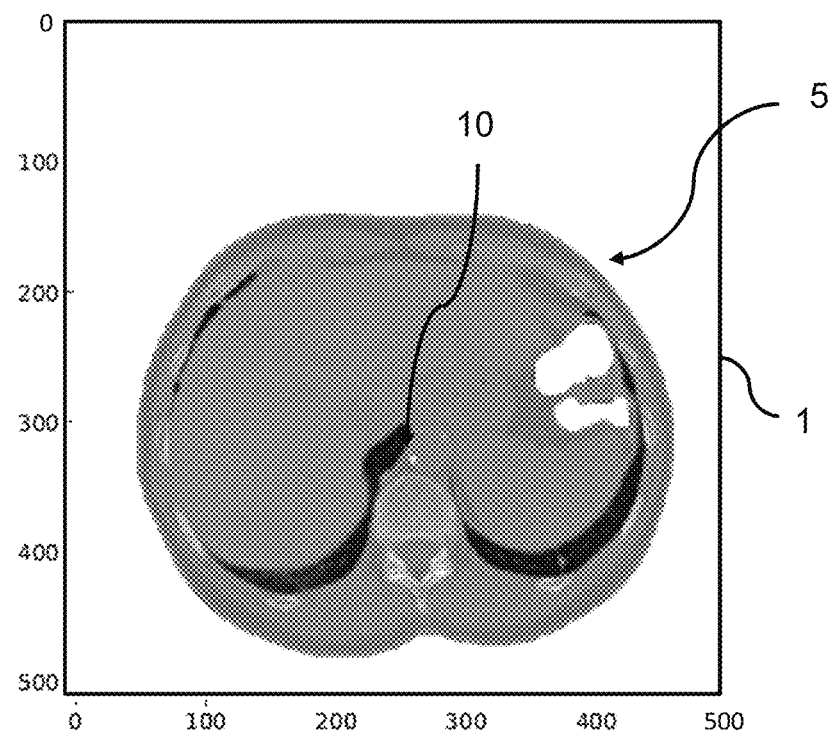
FIG. 1 illustrates a 2-dimensional slice of a computed tomography scan of a blood vessel having a lesion.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The present invention provides a method, computer program and processing system for identifies boundaries of lesions within image data. The image data is processed using a machine learning algorithm to generate probability data and uncertainty data. The probability data provides, for each image data point of the image data, a probability data points indicating a probability that said image data point is part of a lesion. The uncertainty data provides, for each probability data point, an uncertainty data point indicating an uncertainty of the said probability data point. The uncertainty data is processed to identify or correct boundaries of the lesions.

The inventive concept is based on the realization that boundaries of lesions can be more accurately identified by processing or further analysis of uncertainty data indicating an uncertainty of a prediction that a particular image data point is or isn't part of a lesion.

Embodiments may be employed in the identification of lesions within a medical image of a subject. By way of example, embodiments may be employed to identify calcium lesions within heart vessels or tumors within a lung or lungs.

As previously described, embodiments relate to concepts for identifying one or more boundaries of lesions within N-dimensional medical image data.

FIG. 1 illustrates an example of a medical image 1 for understanding a context of the invention. Here, the medical image is a 2-dimensional slice of a CT scan of a blood vessel 5, namely the aorta, having a lesion 10. The lesion 10 has a boundary (or boundaries) which can be identified by employing the inventive concept described herein.

A boundary distinguishes portions of the image data that are considered to be part of a lesion ("lesion portions") from portions of the image data that are not considered to be part of a lesion ("non-lesion portions"). In particular, a boundary may go around or define the perimeter of a lesion portion.

A boundary may, for example, be presented in the form of a graphical annotation that can overlay the medical image 1, e.g. on a display, to thereby draw attention to the location of the boundary with respect the image data. In another example, a boundary may be presented in the form of co-ordinate information identifying the location of the bounds of a lesion portion.

Whilst only a 2-dimensional slice of a CT scan is illustrated here, embodiments of the invention may expand to any N-dimensional medical image data, e.g. data for a 3-dimensional CT scan, an ultrasound image, an X-ray image and so on. Medical image data is any data suitable for (re)constructing a visual representation of (an interior or exterior of) a subject for the purposes of analysis by a clinician.

Figure 2:
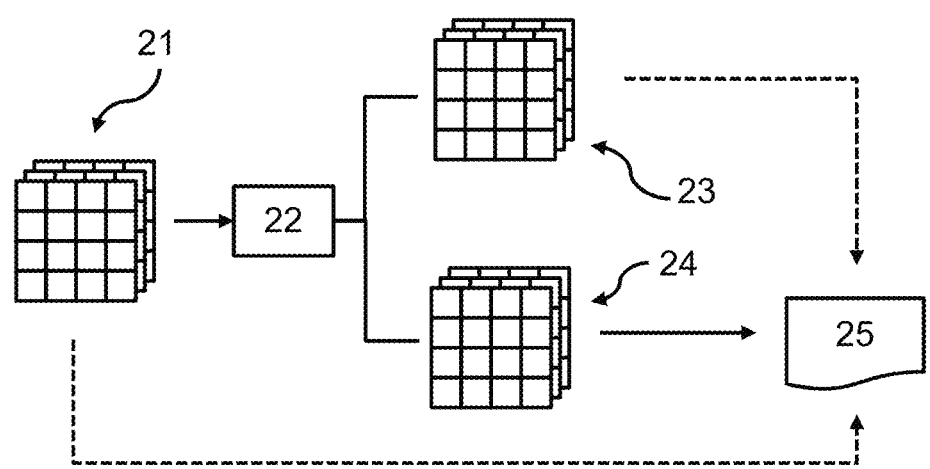
FIG. 2 conceptually illustrates an embodiment of the invention.

FIG. 2 illustrates an underlying concept of the invention, for the purposes of improved understanding of the inventive concept.

Embodiments relate to identifying one or more boundaries of lesions within N-dimensional medical image data 21. The medical image data 21 is formed of image data points, e.g. pixels or voxels, which form an overall N-dimensional image. The medical image data may correspond to a two-dimensional (2D) image or a three-dimensional (3D) image, as illustrated.

The medical image data 21 is processed by a machine learning algorithm 22 to generate probability data 23 and uncertainty data 24. The probability data 23 and uncertainty data 24 have a same number of dimensions, N, as the medical image data 21.

The probability data 23 comprises probability data points. Each probability data point corresponds to a respective image data point, and is indicative of a probability that the respective image data point forms part of a lesion, such as a tumor or calcium deposit. Thus, there are a same number of probability data points as there are image data points.

By way of example, each probability data point may be a continuous value between 0 and 1 directly indicating a probability that the respective image data point is part of a lesion, or may be a binary value (e.g. either 0 or 1) indicating whether or not it is predicted that the respective image data point forms part of a lesion (e.g. is associated with a probability above a threshold probability value). Other suitable formats or values for a probability data point will be apparent to the skilled person.

The uncertainty data 24 comprises uncertainty data points. Each uncertainty data point corresponds to a respective probability data point (and therefore a respective image data point). Each uncertainty data point is indicative of a level of uncertainty of the indicated probability, e.g. a measure or value representing a (un)certainty that the probability data point is correct. Thus, there are a same number of uncertainty data points as there are probability data points, and therefore of image data points.

By way of example, each uncertainty data point may be a continuous value between 0 and 1 indicating a measure of relative uncertainty that the probability data point is correct. In another example, each uncertainty data point may indicate a margin of error or standard deviation of the probability data point (e.g. if the probability data point is a continuous value between 0 and 1). Other suitable formats or values for an uncertainty data point will be apparent to the skilled person.

The uncertainty data is then used to identify or correct boundaries of the lesions within the medical image. The identified boundaries may be provided as boundary data 25, e.g. identifying locations of boundaries within the image data 21. By way of example, the boundary data may identify co-ordinates of a boundary or boundaries within the image data, or may indicate which image data points are part of a boundary.

It will be generally appreciated that the probability data could itself be used to define predicted locations of a boundary (or boundaries) of a lesion or lesions. This is because the probability data can be used to predict whether a given image data point is part of a lesion. Thus, a perimeter of a lesion can be identified using the probability data.

By way of example only, if a probability data point is a continuous value between 0 and 1, a given image data point may be considered to be part of a lesion if that image data point is associated with a probability data point greater than a predetermined value, and not otherwise. By way of another example, if a probability data point is a binary (e.g. 0 or 1) prediction, a given image data point may be considered to be part of a lesion if that image data point is associated with a probability data point of 1, and not otherwise.

In this way, the probability data can be used to identify potential lesions within the image data.

The present invention relies on the understanding that the probability data may not be completely accurate when predicting whether a given image data point is part of a lesion or not. Indeed, the present invention recognizes that the level of accuracy reduces near the boundary or edge of a lesion.

The inventors have recognized that uncertainty data can be used to more accurately identify where a boundary of a lesion lies with respect to the image data.

In particular embodiments, the uncertainty data can be used to perform further processing to identify a location of a boundary with more accuracy than the probability data alone. Identifying a location of a boundary may comprise correcting a location of a predicted boundary derived from the probability data.

Figure 3:
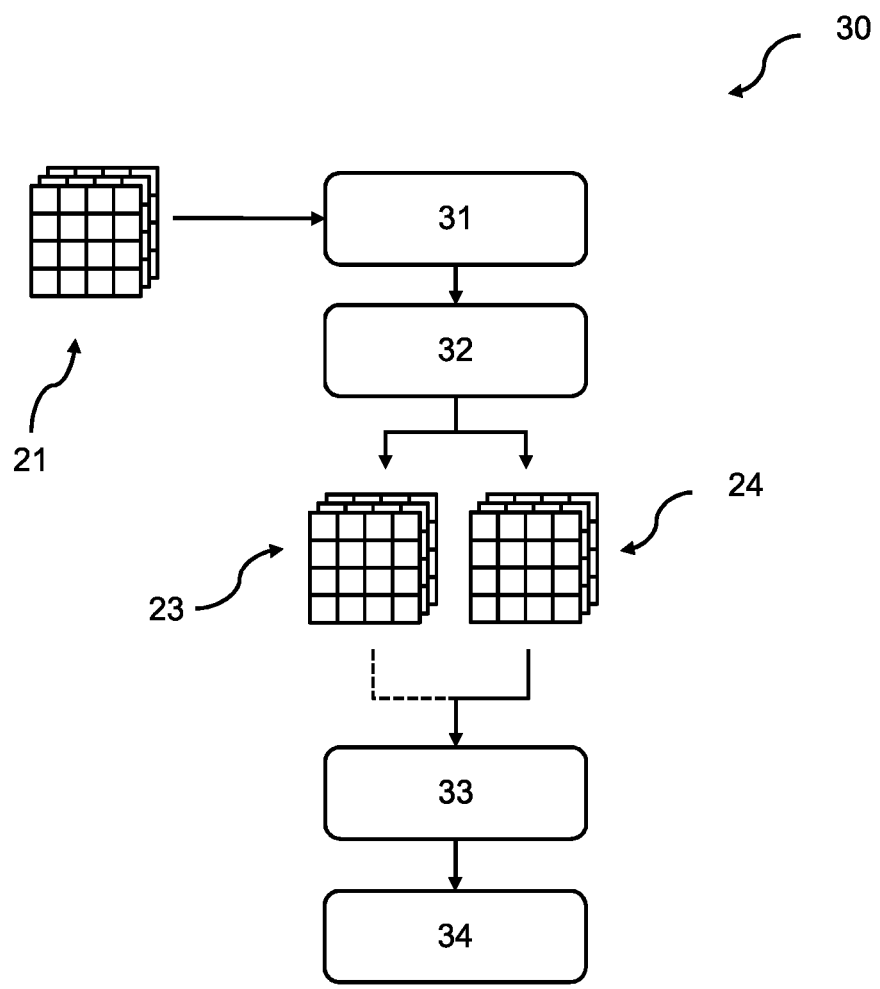
FIG. 3 is a flowchart illustrating a method according to an embodiment.

FIG. 3 illustrates a method 30 according to an embodiment of the invention. The method identifies one or more boundaries of lesions within N-dimensional medical image data of a region of a subject, The method 30 comprises a step 31 of receiving the N-dimensional medical image data, comprising image data points.

The method 30 further comprises a step 32 of processing the N-dimensional medical image data, using a machine-learning algorithm, to thereby generate N-dimensional probability data and N-dimensional uncertainty data. The N-dimensional probability data comprises a respective probability data point for each image data point indicating a probability that the image data point is part of a lesion. The N-dimensional uncertainty data comprises a respective uncertainty data point for each probability data point indicating an uncertainty of the indicated probability.

The method 30 further comprises a step 33 of identifying one or more boundaries of lesions in the medical image data using at least the uncertainty data.

Step 33 may be implemented in a number of different possible ways.

In particular, step 33 may comprise identifying one or more potential lesions in the medical image data based on the probability data and processing each potential lesion using at least the uncertainty data to identify one or more boundaries of lesions in the medical image data.

Thus, an initially predicted lesion can be identified based on the probability data. The boundaries of this lesion may be modified based on at least the uncertainty data.

The boundaries of the lesion may be modified in an automated fashion, using a region growing algorithm and/or a region shrinking algorithm.

A region growing method can be used to expand the size of an initial lesion by using a set of rules to decide whether the neighboring image data points (i.e. image data points neighboring image data points of the predicted lesion) should be added to the lesion.

Region growing methods can be based on values or magnitudes (e.g. the Hounsfield Unit) of the neighboring image data points, with the decision rule (i.e. to include or not include the image data point in the lesion) being a simple inclusion threshold magnitude of the image data point. Thus, if a magnitude of a neighboring image data point is above an inclusion threshold value, then that neighboring image data point is included in the potential lesion.

One approach to implement this could be to change the inclusion threshold based on the level of uncertainty for the same image data point or an average uncertainty of the associated predicted lesion. The thresholds can be parameters that are tuned during the hyperparameter optimization of the segmentation model.

The region growing algorithm may be stopped when the predicted lesion is unable to grow any further, i.e. when there are no new pixels that neighbor a (updated) predicted lesion.

Figure 4:
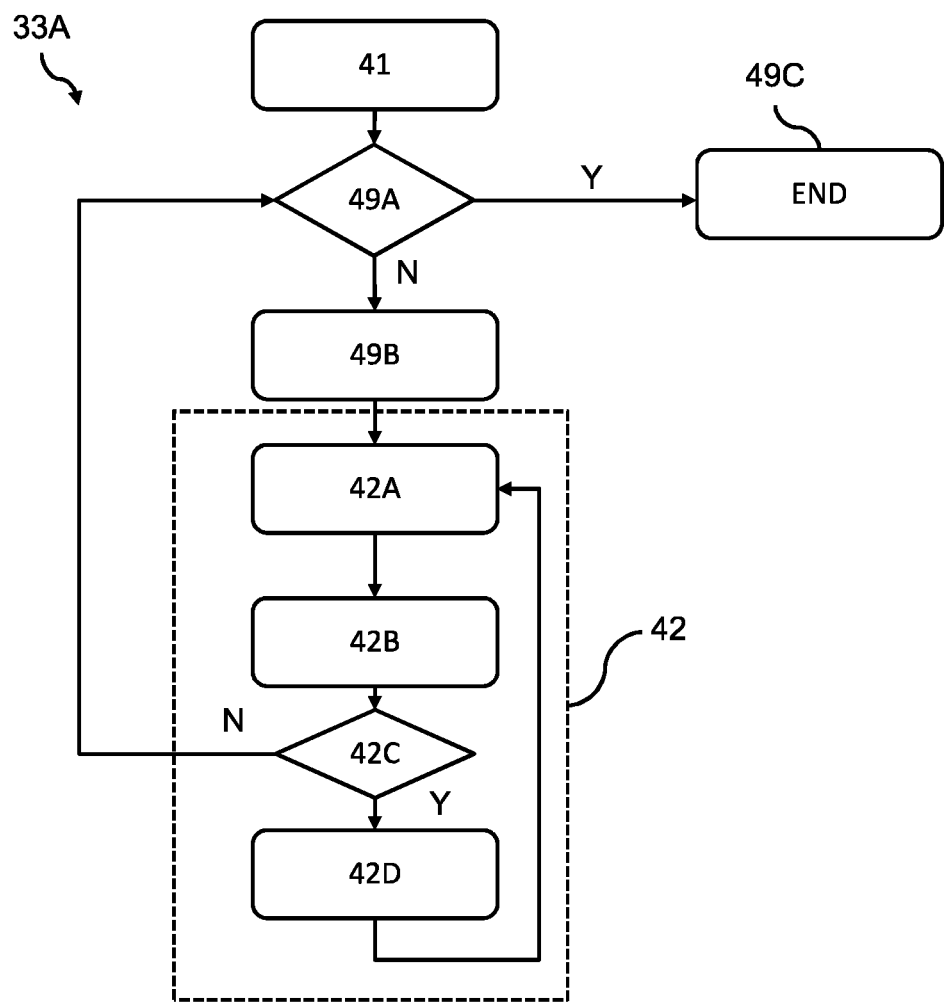
FIG. 4 illustrates a region growing algorithm for use in an embodiment.

FIG. 4 illustrates an example method 33A of step 33 in which a region growing algorithm 42 is performed.

The method 33A comprises a step 41 of identifying one or more potential lesions in the medical image data based on the probability data.

Step 41 may comprise identifying sets of image data points associated with a probability data point indicating that the probability (that the image data point forms part of a lesion) is above a predetermined probability value. Other methods of identifying a potential lesion using probability data will be known to the skilled person.

Step 41 may comprise a substep (not shown) of selectively rejecting (i.e. excluding from further consideration) potential lesions based on the uncertainty data. For example, if image data points forming a potential lesion are associated with an average uncertainty above a predetermined value, the potential lesion may be rejected (i.e. removed from the one or more potential lesions). As another example, if more than a certain percentage of image data points forming a potential lesion are associated with an uncertainty data point having an uncertainty above a predetermined value, then this potential lesion can be rejected. This improves the accuracy in correctly identifying potential lesions, in particular the true positive rate, by rejecting those lesions that are uncertainly predicted.

A region growing algorithm is then applied to each identified potential lesion. This may be performed in parallel or consecutively. In the illustrated embodiment, each region growing algorithm is applied consecutively to each identified potential lesion. Thus, there is a step 49A of determining whether there are any unprocessed potential lesions (i.e. lesions to which the region growing algorithm has not been applied). The method 33A ends in step 49C if each potential lesion has been processed. If each potential lesion has not been processed, then step 49D of selecting an unprocessed lesion is performed.

An embodiment of a region growing algorithm 42 is hereafter provided.

The region growing algorithm 42 comprises a step 42A of identifying perimeter image data points that form the perimeter of the potential lesion. The perimeter image data points are the outermost image data points of the potential lesion, i.e. image data points that border, abut, are adjacent to or immediately neighbor image data points that do not form part of the potential lesion.

The region growing algorithm 42 further comprises a step 42B of identifying neighboring image data points, being image data points external to the potential lesion and immediately adjacent to any of the perimeter image data points. Thus, each neighboring image data point in an image data point that abuts an image data point of a potential lesion.

The region growing algorithm 42 ends in response to no new neighboring image data points being identified in step 42B. Thus, there may be a step 42C of determining whether any new neighboring image data points have been identified.

If new neighboring image data points have been identified, e.g. in step 42C, the region growing algorithm 42 moves to a step 42D of adding any neighboring image data point to the potential lesion that have a magnitude greater than a first magnitude threshold value for that neighboring image data point. This effectively grows the size of the potential lesion.

The first magnitude threshold value is based upon the uncertainty data point associated with the neighboring image data point. Thus, the first magnitude threshold value may differ for each neighboring image data point.

By way of example, a value of the uncertainty data point may act as a variable for an equation that calculates the first magnitude threshold value. In one example, the uncertainty data point is used to modify a predetermined value for the magnitude threshold value to generate the first magnitude threshold value. As another example, the first magnitude threshold value of each neighboring image data point can be parameters that are generated during generation of the uncertainty data (i.e. by the machine-learning algorithm). Thus, each image data point may be associated with a respective first magnitude threshold value (generated by the machine-learning algorithm) for use with the region growing algorithm.

The region growing algorithm is iteratively repeated until no new neighboring image data points are identified, i.e. the lesion stops growing.

Referring back to FIG. 3, step 33 may comprise performing a region shrinking or region reducing algorithm. This may be performed instead of, or in addition to, the region growing algorithm.

The region shrinking algorithm is similar to the region growing algorithm except that it is used to reduce the size of a lesion. This may be performed, for example, by inspecting the image data points that form the perimeter of the lesion and applying the decision rules that combine the magnitudes of the image data points and inclusion thresholds based on uncertainty data. The region shrinking algorithm may be stopped when the predicted lesion is unable to shrink any further, e.g. when all image data points forming the perimeter of the lesion have a magnitude above their respective thresholds.

Figure 5:
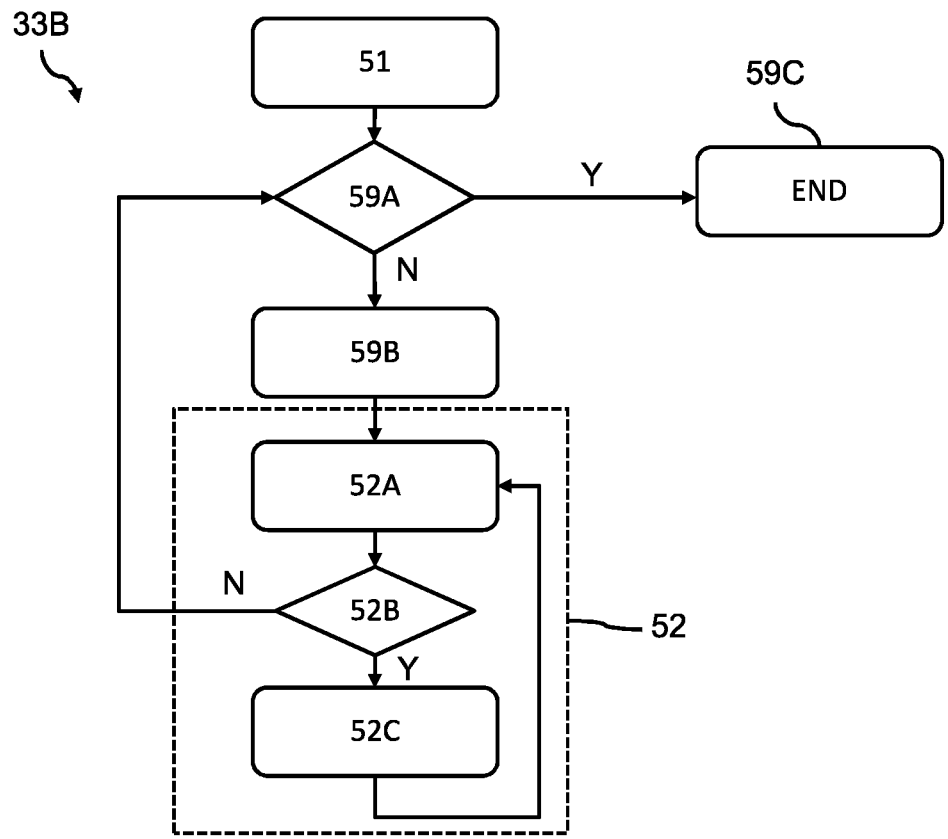
FIG. 5 illustrates a region shrinking algorithm for use in an embodiment.

FIG. 5 illustrates an example method 33B of step 33 in which a region shrinking algorithm is performed.

The method 33B comprises a step 51 of identifying one or more potential lesions in the medical image data based on the probability data, in a substantially identical manner to step 41 of method 33A. Step 51 may be performed at the same time as step 41 (if performed).

A region shrinking algorithm 52 is applied to each identified potential lesion. This may be performed in parallel or consecutively. In the illustrated embodiment, each region shrinking algorithm is applied consecutively to each identified potential lesion. Thus, there is a step 59A of determining whether there are any unprocessed potential lesions (i.e. lesions to which the region shrinking algorithm has not been applied). The method 33B ends in step 59C if each potential lesion has been processed. If each potential lesion has not been processed, then step 59D of selecting an unprocessed lesion is performed.

The region shrinking algorithm 52 comprises a step 52A of identifying perimeter image data points that form the perimeter of the potential lesion. As before, the perimeter image data points are the outermost image data points of the potential lesion, i.e. image data points that border, abut, are adjacent to or immediately neighbor image data points that do not form part of the potential lesion.

The region growing algorithm 52 ends in response to no new perimeter image data points being identified in step 52A. Thus, there may be a step 52B of determining whether any new perimeter image data points have been identified. If no new perimeter image data points have been identified, the region shrinking algorithm ends.

If new perimeter image data points have been identified, then step 52C is performed. Step 52C comprises removing any perimeter image data point from the potential lesion that have a magnitude less than a second magnitude threshold value for the perimeter image data point. The second magnitude threshold value is based upon the uncertainty data point associated with the perimeter image data point.

The second magnitude threshold value is based upon the uncertainty data point associated with the neighboring image data point. Thus, the second magnitude threshold value may differ for each neighboring image data point.

By way of example, a value of the uncertainty data point may act as a variable for an equation that calculates the second magnitude threshold value. In one example, the uncertainty data point is used to modify a predetermined value for the magnitude threshold value to generate the second magnitude threshold value. As another example, the second magnitude threshold value of each neighboring image data point can be parameters that are generated during generation of the uncertainty data (i.e. by the machine-learning algorithm). Thus, each image data point may be associated with a respective second magnitude threshold value (generated by the machine-learning algorithm) for use with the region growing algorithm. The first and second magnitude threshold values may be the same.

Referring back to FIG. 3, in another example, step 33 comprises presenting predicted boundary portions to a user, and enabling the user to indicate corrections or modifications to the predicted boundary portions. Thus, identifying a boundary may comprise receiving a user input indicating one or more boundaries of a lesion (which input is received after presenting predicted boundary portions to a user).

In some embodiments, the user may be able to reject presented boundaries, thereby rejecting a predicted lesion.

In particular step 33 may comprise identifying one or more predicted boundary portions of each potential lesion using the probability data, each predicted boundary portion being a predicted location of a portion of a boundary of the potential lesion; identifying an uncertainty of each predicted boundary portion and/or an uncertainty of each potential lesion using the uncertainty data; selecting one or more of the predicted boundary portions based on the identified uncertainty of each boundary portion and/or an uncertainty of each potential lesion; presenting the selected predicted boundary portions to a user; after presenting the selected predicted boundary portions to the user, receiving a user input indicating one or more boundaries of lesions; and identifying the boundary portions based on the received user input.

In this way, the method may exploit a clinician's understanding and experience to more accurately identify boundaries, without placing a burden on the clinician of identifying where automatically predicted boundaries need to be corrected. In particular, by drawing attention to the most (or least) uncertain predicted boundaries, the clinician is not required to correct boundaries that are considered to be identified with sufficient accuracy. This increases an ease and speed of identifying boundaries within image data.

It is possible to consider two levels of uncertainties, one being the uncertainty of the whole potential lesion ("lesion uncertainty") and the other being the uncertainty of a boundary portion ("boundary uncertainty"). Each boundary portion can be associated with a lesion uncertainty and a boundary uncertainty. The lesion uncertainty may, for example, be an average uncertainty associated with each image data point of the potential lesion or a relative number (e.g. percentage) of the image data points of the potential lesion having an uncertainty above a certain threshold value. The boundaries selected for being presented to the user may depend upon one or both of these uncertainty measures.

For example, the boundaries selected for presentation may be those associated with a boundary uncertainty above a first predetermined uncertainty value and a lesion uncertainty below a second predetermined uncertainty value. The first and second predetermined uncertainty values may be the same. The first and second predetermined uncertainty values are preferably in the range of 40-70% of the maximum possible uncertainty value.

In another example, the boundaries selected for presentation may be those associated with a lesion uncertainty above a third predetermined uncertainty value. Thus, boundaries for lesions that are uncertain may be presented to a user for modification and/or rejection.

Thus, generally speaking, the probability and uncertainty data can be used to either expand the detected lesions in an automated manner by combining the uncertainty data with a region growing algorithm, or in a semi-automated manner where the least uncertain borders of lesions are presented to a clinician or user to allow for efficient corrections of any misidentification of boundaries.

Referring back to FIG. 3, the method 30 may further comprise a step 34 of generating a respective one or more graphical annotations, each indicating a location of each one or more identified boundaries.

Thus, for each identified boundary, a graphical annotation may be generated that identifies the location and extend of the identified boundary. This graphical annotation may be designed to overlay the image data (e.g. on a display) so as to indicate the location and/or presence of a boundary of a lesion. The graphical annotations may be contained in boundary data.

In some embodiments, the method may further comprise displaying the N-dimensional image data and the one or more graphical annotations, e.g. on a display. This display enables attention to a boundary of a lesion to be drawn to the attention of a subject.

The proposed invention enables more accurate identification of boundaries of lesions. This directly aids a user in the performance of a task of diagnosing or assessing a condition of the subject, as there will be more accurate identification of the number, location and size of lesions within the subject.

Thus, the proposed invention provides a credible assistance to the user in the performance of a technical task (e.g. of diagnosing or otherwise assessing a condition of a subject/patient). In particular, more accurate identification of a boundary of a lesion is performed, improving the information that is made available to a clinician.

The proposed invention also recognizes that a direct link can be made between the actual location of a lesion boundary and the uncertainty in a predicted location of the lesion boundary.

It will be understood that a machine-learning algorithm is any self-training algorithm that processes input data in order to produce output data. In the context of the present invention, the input data comprises N-dimensional image data and the output data comprises N-dimensional probability data and N-dimensional uncertainty data.

Suitable machine-learning algorithms for being employed in the present invention will be apparent to the skilled person. Examples of suitable machine-learning algorithms include decision tree algorithms, artificial neural networks, logistic regression or support vector machines.

Preferably, the machine-learning algorithm is a Bayesian deep learning segmentation algorithm, such as a Bayesian neural network. Bayesian-based machine-learning models provide a relatively simple method of calculating the uncertainty of a probability data point, as uncertainty calculation is built into the Bayesian methodology.

The structure of an artificial neural network (or, simply, neural network) is inspired by the human brain. Neural networks are comprised of layers, each layer comprising a plurality of neurons. Each neuron comprises a mathematical operation. In particular, each neuron may comprise a different weighted combination of a single type of transformation (e.g. the same type of transformation, sigmoid etc. but with different weightings). In the process of processing input data, the mathematical operation of each neuron is performed on the input data to produce a numerical output, and the outputs of each layer in the neural network are fed into the next layer sequentially. The final layer provides the output.

Methods of training a machine-learning algorithm are well known. Typically, such methods comprise obtaining a training dataset, comprising training input data entries and corresponding training output data entries. In the context of the present invention, the training input data entries correspond to example N-dimensional image data. The training output data entries correspond to boundaries of lesions within the N-dimensional image data (which effectively identifies a probability that a given image data point of the image data forms part of a lesion).

An initialized machine-learning algorithm is applied to each input data entry to generate predicted output data entries. An error or loss function between the predicted output data entries and corresponding training output data entries is used to modify the machine-learning algorithm. This process can repeated until the error converges, and the predicted output data entries are sufficiently similar (e.g. ±1%) to the training output data entries. This is commonly known as a supervised learning technique.

In a Bayesian neural network, each weight is associated with a probability distribution. During training of the Bayesian neural network, the probability distributions of the weights can be updated to reflect the latest teaching of the training data. This effectively provides a model having its own probability distribution, which can thereby output predicted data having a probability distribution for each data point.

In such examples, a probability data point may be the mean or central probability of the probability distribution and an uncertainty data point may be a standard deviation of the probability distribution. This provides a simple, effective and low-cost processing method for generating the probability and uncertainty data.

In the context of the present invention, the machine-learning algorithm may be trained using a loss function that accounts for the fact that the predicted lesions should form connected components and that the uncertainty estimate should focus on the borders of the lesions.

One example of a suitable loss function is shown in equation (1) below.

$$\mathrm{Loss}(P,G) = \mathrm{Dice}(P,G) + \gamma \mathrm{CCscore}(P) \qquad (1)$$

In equation 1, P denotes the probability data point predictions for the image data, G denotes the ground truth, Dice is the dice similarity coefficient between the model predictions and the ground truth and CCscore is a measure of whether the predicted lesions are compact or have missing pixels. CCscore can be measured by creating a fully compact lesion from the predictions (i.e. by adding the missing pixels from a predicted lesion) and then measuring the difference (e.g. in number of pixels) between this compact lesion to the predicted one. $\gamma$ is a real number providing a weight to this part of the loss function and is optimized during the training of the model.

From the foregoing, it is apparent that the machine-learning algorithm is trained to directly calculate the probability data from the image data.

The uncertainty data can be calculated using the Monto Carlo dropout approach. In particular, the machine-learning model can be trained with dropout layers in the model architecture. During inference of the probability data, we have dropout "turned on", meaning that if the inference is run multiple times, then we will get different probability data (i.e. different predictions). Uncertainty can then be measured as the variance of these predictions. The skilled person would know other methods of calculating uncertainty data.

Further information on Bayesian Deep Learning models and uncertainty information is found in the paper by Kendall, Alex, and Yarin Gal. "What uncertainties do we need in bayesian deep learning for computer vision?." Advances in neural information processing systems. 2017. The skilled person would consider consulting this document to identify further information on Bayesian Deep Learning models.

The skilled person would be readily capable of developing a processing system for carrying out any herein described method. Thus, each step of the flow chart may represent a different action performed by a processing system, and may be performed by a respective module of the processing system.

Figure 6:
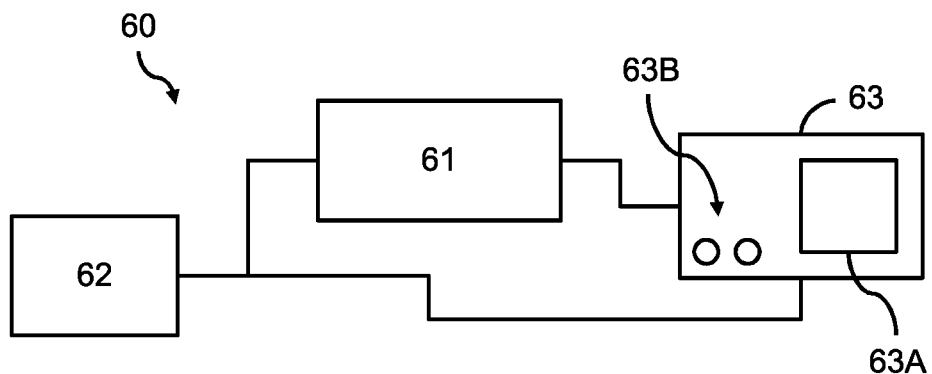
FIG. 6 illustrates a system according to an embodiment.

FIG. 6 illustrates a system 60 in which a processing system 61 according to an embodiment is implemented. The system comprises the processing system 61, an image data generator 62 and a display unit 63.

The processing system 61 is adapted to receive N-dimensional medical image data, comprising image data points; process the N-dimensional medical image data, using a machine-learning algorithm, to thereby generate: N-dimensional probability data, comprising a respective probability data point for each image data point indicating a probability that the image data point is part of a lesion; and N-dimensional uncertainty data, comprising a respective uncertainty data point for each probability data point indicating an uncertainty of the indicated probability; and identify one or more boundaries of lesions in the medical image data using at least the uncertainty data.

The image data generator 62 is adapted to generate or provide the N-dimensional medical image data. The image data generator may comprise, for example, a memory system storing medical image data (e.g. a bank of medical images) or an image data generating element, such as a CT scanner. The image data generator generates medical image data for analysis by the processing system 61.

The display unit 63 is adapted to receive information about the boundaries identified by the processing system 61 (e.g. boundary information) and display this information, e.g. on a display 63A. The display unit may be adapted to display the medical image data associated with the boundaries, e.g. beneath the illustrated boundaries. This medical image data may be received directly from the image data generator 62

The display unit 63 may further comprise a user interface 63B, which may allow the user to change or manipulate the view of the medical image (and therefore of the visible boundaries), as would be known to the skilled person.

Embodiments therefore make use of a processing system. The processing system can be implemented in numerous ways, with software and/or hardware, to perform the various functions required. A processor is one example of a processing system which employs one or more microprocessors that may be programmed using software (e.g., microcode) to perform the required functions. A processing system may however be implemented with or without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

It will be understood that disclosed methods are preferably computer-implemented methods. As such, there is also proposed the concept of computer program comprising code means for implementing any described method when said program is run on a processing system, such as a computer. Thus, different portions, lines or blocks of code of a computer program according to an embodiment may be executed by a processing system or computer to perform any herein described method. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A method of identifying one or more boundaries of lesions within N-dimensional medical image data of a region of a subject, the method comprising:
   receiving the N-dimensional medical image data, comprising image data points;
   processing the N-dimensional medical image data, using a machine-learning algorithm, to thereby generate:
   N-dimensional probability data, comprising a respective probability data point for each image data point indicating a probability that the image data point is part of a lesion; and
   N-dimensional uncertainty data, comprising a respective uncertainty data point for each probability data point, and thereby each image data point, indicating an uncertainty of probability indicated by the probability data point; and
   identifying one or more boundaries of lesions in the medical image data using at least the probability data and the uncertainty data.

2. The method of claim 1, wherein the step of identifying one or more boundaries of lesions comprises:
   identifying one or more potential lesions in the medical image data based on the probability data; and processing each potential lesion using at least the uncertainty data to identify one or more boundaries of lesions in the medical image data.

3. The method of claim 2, wherein the step of identifying one or more boundaries of lesions comprises applying a region growing algorithm to each potential lesion, the region growing algorithm using the image data and the uncertainty data to thereby define the boundaries of each potential lesion.

4. The method of claim 3, wherein applying the region growing algorithm to each potential lesion comprises iteratively performing, for each potential lesion, steps of:
   identifying perimeter image data points that form the perimeter of the potential lesion;
   identifying neighboring image data points, being image data points external to the potential lesion and immediately adjacent to any of the perimeter image data points; and
   for each neighboring image data point, adding the neighboring image data point to the potential lesion in response to a magnitude of the neighboring image data point being greater than a first magnitude threshold value for that neighboring image data point, wherein the first magnitude threshold value is based upon the uncertainty data point associated with the neighboring image data point, wherein the first region growing algorithm ends in response to no new neighboring image data points being identified.

5. The method of claim 2, wherein the step of identifying one or more boundaries of lesions comprises applying a region shrinking algorithm to each potential lesion, the region shrinking algorithm comprising iteratively performing steps of:
   identifying perimeter image data points that form the perimeter of the potential lesion;
   for each perimeter image data point, removing the perimeter image data point from the potential lesion in response to a magnitude of the perimeter image data point being less than a second magnitude threshold value for the perimeter image data point,
   wherein the second magnitude threshold value is based upon the uncertainty data point associated with the perimeter image data point, wherein the second region growing algorithm ends in response to no new perimeter image data points being identified.

6. The method of claim 2, wherein the step of identifying one or more boundaries of lesions comprises:
   identifying one or more predicted boundary portions of each potential lesion using the probability data, each predicted boundary portion being a predicted location of a portion of a boundary of the potential lesion;
   identifying an uncertainty of each predicted boundary portion and/or an uncertainty of each potential lesion using the uncertainty data;
   selecting one or more of the predicted boundary portions based on the identified uncertainty of each boundary portion and/or an uncertainty of each potential lesion;

presenting the selected predicted boundary portions to a user;

after presenting the selected predicted boundary portions to the user, receiving a user input indicating one or more boundaries of lesions; and identifying the boundary portions based on the received user input.

7. The method of claim 6, wherein the step of selecting one or more predicted boundary portions comprises selecting those boundary portions associated with an uncertainty above a first predetermined uncertainty value and/or those boundary portions associated with a lesion having an uncertainty below a second predetermined uncertainty value.

8. The method of claim 2, wherein the step of identifying one or more potential lesions in the medical image data comprises identifying groups of image data points associated with a probability data point that indicates that a probability that the image data point is part of a lesion is above a predetermined probability, each group of image data points thereby forming a potential lesion.

9. The method of claim 1, further comprising generating a respective one or more graphical annotations, each indicating a location of each one or more identified boundaries.

10. A non-transitory computer readable medium comprising a computer program for implementing the method of claim 1 when said program is run on a processing system.

11. A processing system for identifying one or more boundaries of lesions within N-dimensional medical image data of a region of a subject, the processing system being adapted to:

receive the N-dimensional medical image data, comprising image data points;

process the N-dimensional medical image data, using a machine-learning algorithm, to thereby generate:

N-dimensional probability data, comprising a respective probability data point for each image data point indicating a probability that the image data point is part of a lesion; and N-dimensional uncertainty data, comprising a respective uncertainty data point for each probability data point indicating an uncertainty of the indicated probability;

and identify one or more boundaries of lesions in the medical image data using at least the probability data and the uncertainty data.

12. The processing system of claim 11, wherein the processing system is adapted to:

identify one or more potential lesions in the medical image data based on the probability data; and process each potential lesion using at least the uncertainty data to identify one or more boundaries of lesions in the medical image data.

13. The processing system of claim 12, wherein the processing system is adapted to process each potential lesion by applying a region growing algorithm to each potential lesion, the region growing algorithm using the image data and the uncertainty data to thereby define the boundaries of each potential lesion.

14. The processing system of claim 12, wherein the processing system is adapted to process each potential lesion by:

identifying one or more predicted boundary portions of each potential lesion using the probability data, each predicted boundary portion being a predicted location of a portion of a boundary of the potential lesion;

identifying an uncertainty of each predicted boundary portion and/or an uncertainty of each potential lesion using the uncertainty data;

selecting one or more of the predicted boundary portions based on the identified uncertainty of each boundary portion and/or an uncertainty of each potential lesion;

presenting the selected predicted boundary portions to a user;

after presenting the selected predicted boundary portions to the user, receiving a user input indicating one or more boundaries of lesions; and identifying the boundary portions based on the received user input.

15. The processing system of claim 11 further adapted to generate a respective one or more graphical annotations, each indicating a location of each one or more identified boundary.

16. A method implemented by a processing system, the method comprising:

receiving, by the processing system, N-dimensional medical image data, comprising a plurality of image data points;

generating, by the processing system:

N-dimensional probability data, comprising probability data points respective to the image data points in the plurality, wherein the probability data points indicate a probability that the image data points are part of a lesion; and N-dimensional uncertainty data, comprising uncertainty data points respective to the probability data points in the plurality; and identifying, by the processing system, one or more boundaries of lesions in the medical image data using at least the probability data points and the uncertainty data points.

17. The method of claim 16, wherein identifying one or more boundaries of lesions further comprises applying a region growing algorithm using the image data and the uncertainty data to define the boundaries of at least one potential lesion.

18. A non-transitory computer readable medium comprising a computer program for implementing the method of claim 16 when said program is run on the processing system.

19. A non-transitory computer readable medium comprising a computer program for implementing the method of claim 17 when said program is run on the processing system.

20. The processing system for identifying one or more boundaries of lesions within N-dimensional medical image data of a region of a subject, the processing system being adapted to perform the steps of claim 16.

* * * * *